US00PP35963P2

(12) United States Plant Patent
Weis

(10) Patent No.: US PP35,963 P2
(45) Date of Patent: Jul. 2, 2024

(54) ***LAVANDULA* PLANT NAMED 'ST 18-29'**

(50) Latin Name: *Lavandula stoechas*
Varietal Denomination: ST 18-29

(71) Applicant: PLANTINOVA SL, Cabrils (ES)

(72) Inventor: Charlotte Weis, Horsens (DK)

(73) Assignee: PLANTINOVA SL, Cabrils (ES)

( * ) Notice: Subject to any disclaimer, the term of this patent is extended or adjusted under 35 U.S.C. 154(b) by 0 days.

(21) Appl. No.: 18/242,325

(22) Filed: Sep. 5, 2023

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./445
CPC ... A01H 5/02; A01H 5/12; A01H 5/00; A01H 6/50; A01H 6/502
See application file for complete search history.

(56) References Cited

U.S. PATENT DOCUMENTS

PP33,269 P2 * 7/2021 Koning ..... A01H 6/502 Plt./445

OTHER PUBLICATIONS

Perishable News. Plant Development Services Announces CAST 2023 New Releases retrieved on Nov. 13, 2023 at https://www.perishablenews.com/floral/plant-development-services-announces-cast-2023-new-releases/, 2 pp. (Year: 2023).*

Plantinova *Lavandula stoechas* retrieved on Nov. 13, 2023 at https://plantinova.com/our-collections-plantinova/flowering-gardens-collection/lavandula-stoechas/, one page. (Year: 2023).*

* cited by examiner

*Primary Examiner* — June Hwu

(74) *Attorney, Agent, or Firm* — Penny J. Aguirre

(57) ABSTRACT

A new cultivar of *Lavandula* plant named 'ST 18-29' that is characterized by its medium sized stature, its showy inflorescence bracts that are large in size and highly undulate (ruffled), its showy inflorescence bracts that are vibrant lilac in color when opening and plum purple in color when they mature, its uniform and rounded plant shape, its floriferous blooming habit, and its airy plant habit making it easy to transport.

3 Drawing Sheets

Botanical classification: *Lavandula stoechas*.
Variety denomination: 'ST 18-29'.

BACKGROUND OF THE INVENTION

The present invention relates to a new and distinct cultivar of *Lavandula stoechas* and will be referred to hereafter by its cultivar name, 'ST 18-29'. 'ST 18-29' is a new variety of Spanish lavender suitable for landscape and container use.

The new cultivar arose from an ongoing breeding program conducted by the Inventor in Barcelona, Spain. The goal of the breeding program is to develop new cultivars of *Lavandula stoechas* that have strong and dependable plant habits with flowers with showy bracts and intense flower coloration. 'ST 18-29' originated as a seedling that arose in the Inventor's trial plot from seed planted from open pollination in 2017 of unnamed and unpatented proprietary plants of *Lavandula stoechas* from the Inventors breeding program. The specific parents are unknown. The new *Lavandula* was selected as a single unique plant in 2019 from amongst the resulting seedlings.

Asexual propagation of the new cultivar was first accomplished by stem cuttings under the direction of the Inventor in January of 2020 in Watsonville, California. Asexual propagation by stem cuttings has shown that the characteristics of the new cultivar are stable and are reproduced true to type in successive generations.

SUMMARY OF THE INVENTION

The following traits have been repeatedly observed and represent the characteristics of the new lavender. These attributes in combination distinguish 'ST 18-29' as a unique cultivar of *Lavandula*.

1. 'ST 18-29' exhibits a medium sized stature.
2. 'ST 18-29' exhibits showy inflorescence bracts that are large in size and highly undulate (ruffled).
3. 'ST 18-29' exhibits showy inflorescence bracts that are vibrant lilac in color when opening and plum purple in color when they mature.
4. 'ST 18-29' exhibits a uniform and rounded plant shape.
5. 'ST 18-29' exhibits a floriferous blooming habit.
6. 'ST 18-29' exhibits an airy plant habit making it easy to transport.

'ST 18-29' can be most closely compared to *Lavandula stoechas* cultivars 'Ever Great Blue' (not patented) and 'Anouk Deluxe 1225' (U.S. Plant Pat. No. 33,269). 'Ever Great Blue' is similar to 'ST 18-29' in having a floriferous blooming habit and showy flower bracts that are large in size. 'Ever Great Blue' differs from 'ST 18-29' in having inflorescence bracts that are lighter in color, a larger plant size, an earlier blooming time, and inflorescences that are larger in size. 'Anouk Deluxe 1225' is similar to 'ST 18-29' in having showy inflorescence bracts that are purple in color. 'Anouk Deluxe 1225' differs from 'ST 18-29' in having showy inflorescence bracts that are smaller in size and more grey-purple in color and a plant habit that is more upright.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plant Development Services, Sunset Plant Collection, and Pacific Plug & Liner.

BRIEF DESCRIPTION OF THE DRAWINGS

The accompanying color photographs illustrates the overall appearance and distinct characteristics of the new cultivar. The photographs were taken of plants about 8 months in age as grown outdoors in 1-gallon containers in Watsonville, California.

The photograph in FIG. 1 provides a side view of 'ST 18-29' in bloom.

Figure 1:
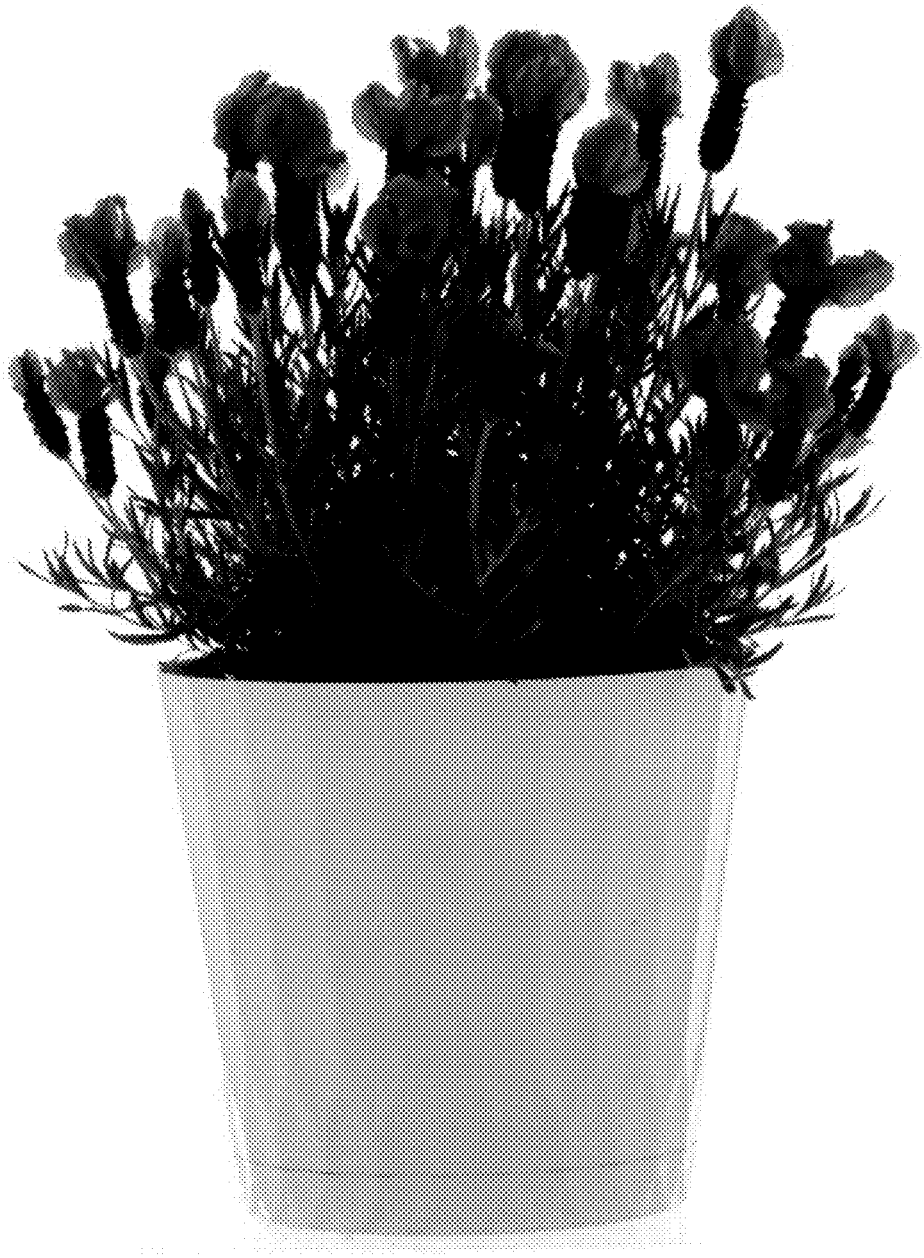
Figure 2:
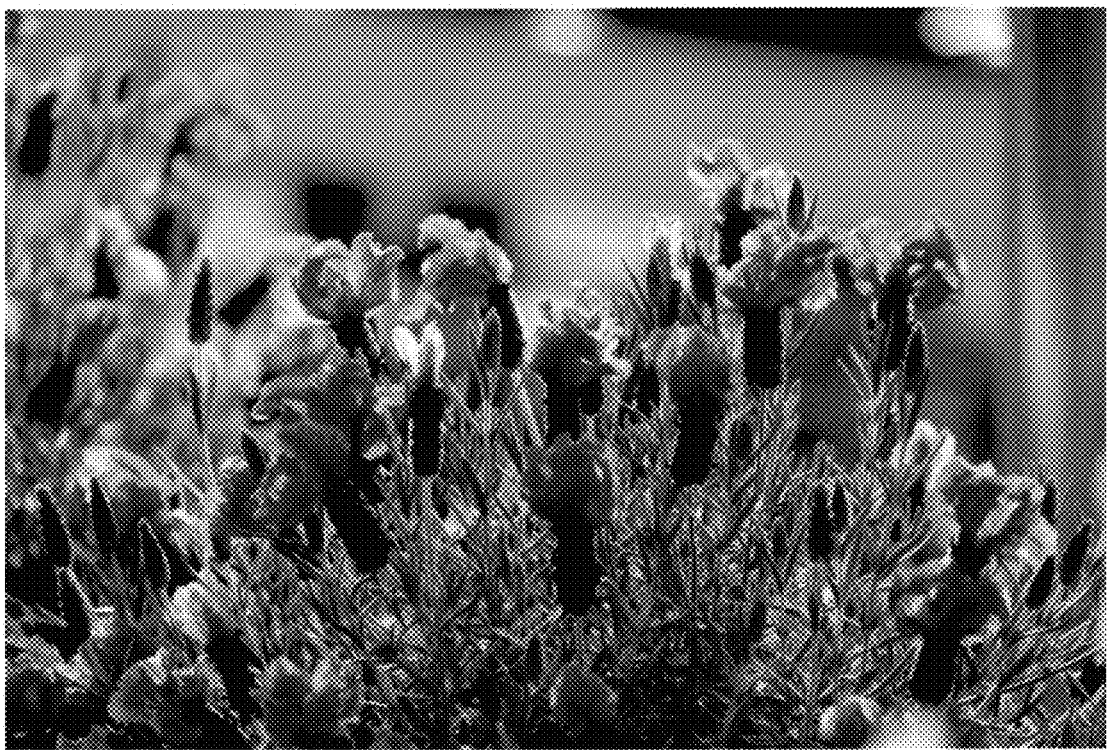

The photograph in FIG. 2 provides a close-up view of an inflorescences of 'ST 18-29'.

Figure 3:
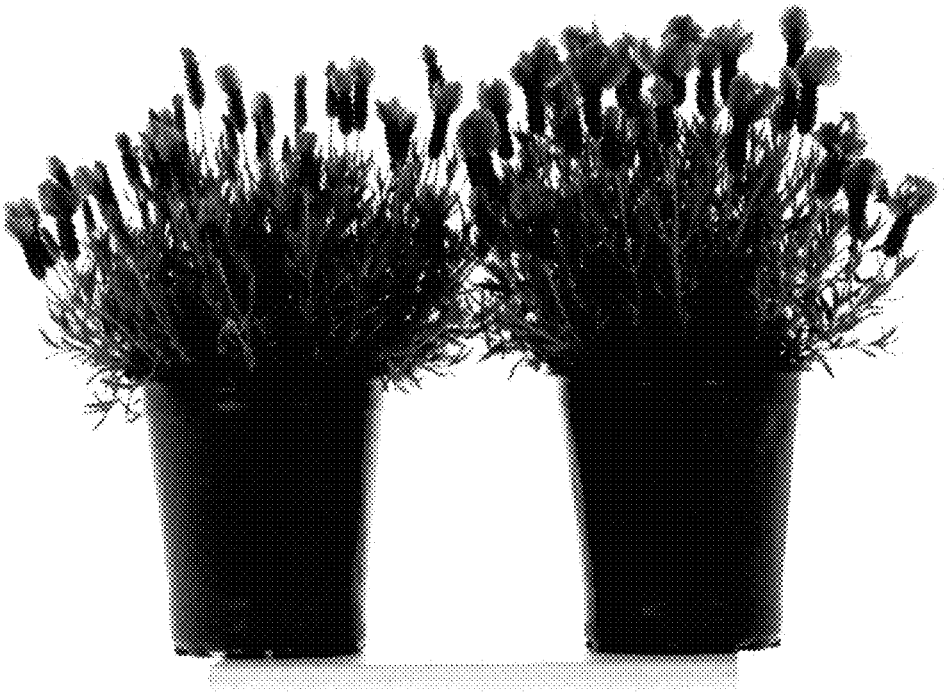

The photograph in FIG. 3 provides a view of 'ST 18-29' young flowers (on the left) and 'ST 18-29' mature flowers (on the right).

Figure 4:
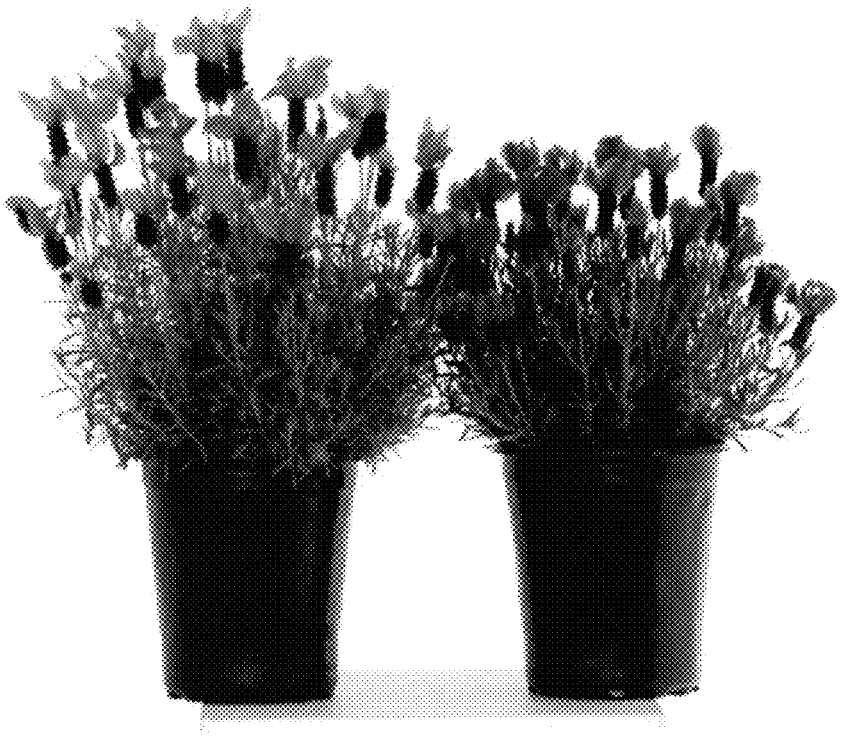

The photograph in FIG. 4 provides a comparison view of 'Ever Great Blue' (on the left) and 'ST 18-29' (on the right).

The colors in the photographs are as close as possible with the photographic and printing technology utilized. The color values cited in the detailed botanical description accurately describe the colors of the new *Lavandula*.

DETAILED BOTANICAL DESCRIPTION

The following is a detailed description of 8-month old plants of the new cultivar as grown outdoors in 1-gallon containers in Watsonville, California. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

- *Blooming habit*.—Mid to late spring and reblooms throughout the summer if cut back when grown in Watsonville, California.
- *Plant type*.—Perennial herb.
- *Plant habit*.—Uniformly rounded with upright lateral branches.
- *Height and spread*.—Reaches an average of 30 cm in height and 25 cm in spread as grown in a garden.
- *Cold hardiness*.—At least to U.S.D.A. Zone 8, although testing in colder zones has not been conducted.
- *Diseases and pests*.—Observed to be relatively disease free, however no particular resistance or susceptibility to diseases or pests has been observed.
- *Root description*.—Densely fibrous, freely branched, 161A in color.
- *Propagation*.—Stem cuttings.
- *Growth*.—Moderately vigorous.
- *Root development*.—An average of 2 weeks for root initiation and 6 to 8 weeks to produce a young plant from a rooted cutting.

Stem description:

- *Stem shape*.—Quadrangular.
- *Stem color*.—Young; 145A, mature; 199A and 199B, old bark; 165A with undertones of 165B.
- *Stem surface*.—Young; glabrous, matte, mature and old bark; moderate striations covering the entire surface, mature stems slightly glossy, old bark dull and dry.
- *Stem size*.—Main stems; 14 cm in length, 8 mm in diameter, lateral stems; 14 cm in length, 4 mm in diameter, tertiary stems; 5 cm in length, 2 mm in diameter.
- *Stem strength*.—Main and lateral stems strong, tertiary stems moderately strong.
- *Branching*.—Freely branched, branches emerge from mounded base, average of 14 main branches, 5 lateral branches per main branch, 8 tertiary branches per lateral branch.

Foliage description:

- *Leaf shape*.—Linear.
- *Leaf division*.—Simple.
- *Leaf base*.—Cuneate.
- *Leaf apex*.—Acute.
- *Leaf venation*.—Both surface; prominent main veins lateral and deeply indented, secondary veins less conspicuous and reticulate, matches surface color with base of veins on both surfaces 189C.
- *Leaf margins*.—Entire.
- *Leaf arrangement*.—Opposite.
- *Leaf attachment*.—Sessile.
- *Leaf number*.—Average of 34 per tertiary branch.
- *Leaf surface*.—Both surfaces are dull, glaucous, soft and densely covered with fine, soft lanate pubescence that matches surface color and too small to measure size.
- *Leaf size*.—Average of 2 cm in length and 2 mm in width.
- *Leaf internode length*.—Average of 2 cm.
- *Leaf color*.—Both surfaces young and mature 189A.
- *Leaf fragrance*.—Strongly fragrant, typical *Lavandula* scent.

Inflorescence description:

- *Inflorescence type*.—Small flowers arranged in compact terminal verticillasters with showy terminal sterile bracts.
- *Inflorescence number*.—1 per tertiary stem.
- *Inflorescence fragrance*.—Strongly fragrant, *Lavandula* scent.
- *Lastingness of inflorescence*.—Average of 10 days.
- *Inflorescence size*.—7 cm in height, 3 cm in diameter.
- *Inflorescence shape*.—Oblong.
- *Plant density at full flower*.—Dense.

*Flowers*.—Outward to upward in aspect, self-cleaning, salverform in shape, with perianth comprised of one upper lip (split into two identical lobes) and one lower lip (split into three lobes), with showy bracts extending from the apex of the inflorescence, 3.5 mm in diameter and 8 mm in height, average of 100 flowers per inflorescence.

*Flower buds*.—Average of 2 cm in length and 3 mm in diameter, narrow oblong in shape, color 145A to 145C, surface is matte, glaucous, densely covered with minute soft lanate pubescence that is translucent to 145D in color.

*Petals*.—Dull and smooth, rotate in arrangement, 2 (upper lip split in 2 lobes, lower lip split in 3 lobes; all lobes are identical in shape and color), spathulate in shape, lower 85% of petals are fused into tube, entire margin, apexes are rounded, length of petal is 7 mm, upper lip is 3 mm in width, lower lip is 3.5 mm in width, color: upper and lower surface when opening and fully opened; N92B, tube is N92B, base is N155A, fading to N186A before drop.

*Sepals*.—3-lobed, serrate margin, acute to apiculate apex, acute base, lobe depth slight, 5 mm in length and 6 mm in width, color; 76C and 159A with veins N89A, glaucous, both surfaces are glaucous, matte, and densely covered with soft lanate pubescence; translucent to NN155C in color.

*Calyx*.—Campanulate in shape, 5 mm in length and 1 cm in diameter.

*Peduncles*.—Moderate in strength, average of 3 cm in length and 2 mm in diameter, held at an average angle of 0° (straight on top of lateral branch), color; 145A, matte and densely covered with soft lanate pubescence; translucent to NN155C in color.

*Pedicels*.—Individual flowers are sessile.

*Bracts*.—Showy, broad rhomboidal to linear in shape, entire and highly undulate (ruffled) margins, rounded to retuse apex, acuminate base, average of 4 cm in length and 3.5 mm in width, color: when opening outer surface; N82A to N82B, veins 83A, base 145D, when opening inner surface; N82B, base 84D, when fully open outer surface; a blend of N78C and 77C, mid-section to top moderately flushed with 93A, veins N92A, base 144C to 144D, when fully open inner surface; a blend of N78A and NN78A, mid-section to top moderately flushed with 93A, veins N92A and 144C, base N142D, both surfaces fade to 77A and N78A, flushed at the top N88A, surfaces are rugose, matte, velvety, and densely covered with soft lanate pubescence that matching the surface color to translucent.

Reproductive organs:

*Pistils*.—1 pistil, stigma; 1 mm in length, narrow, minute and 85C in color, style; 3 mm in length and 85C in color, ovary; NN155C in color.

*Stamens*.—4, anthers; dorsifixed and kidney-shaped, 1 mm in length and 85C in color, filament; into flower tube and 4 mm in length, NN155A in color, pollen moderate in quantity and 26A in color.

*Fruit and seeds*.—No fruit or seed development has been observed to date.

It is claimed:

1. A new and distinct cultivar of *Lavandula* plant named 'ST 18-29' as herein illustrated and described.

* * * * *